United States Patent [19]

Sharma

[11] Patent Number: 4,724,203
[45] Date of Patent: Feb. 9, 1988

[54] CAPROYLAMIDOBIOTINYLATED PEROXIDASE

[75] Inventor: Harmesh K. Sharma, Naperville, Ill.

[73] Assignee: Miles Laboratories, Inc., Elkhart, Ind.

[21] Appl. No.: 784,351

[22] Filed: Oct. 4, 1985

[51] Int. Cl.⁴ .......................... C12Q 1/26; C12N 9/08
[52] U.S. Cl. ..................................... 435/25; 435/192; 435/287
[58] Field of Search .......................... 435/25, 192, 287

[56] References Cited

U.S. PATENT DOCUMENTS 4,282,287  8/1981  Giese .................................. 427/214

OTHER PUBLICATIONS

Costello et al–Clinical Chemistry, vol. 25, No. 9 (1979), pp. 1572-1580.

Primary Examiner—Sam Rosen
Attorney, Agent, or Firm—Louis E. Davidson

[57] ABSTRACT

A new compound, carboylamidobiotinylated horseradish peroxidase, is produced. It has utility in immunohistochemical measurement procedures.

3 Claims, No Drawings

CAPROYLAMIDOBIOTINYLATED PEROXIDASE

BACKGROUND AND DISCUSSION OF PRIOR ART

The bonding reaction between avidin and biotin is well known and forms the basis of various immunoenzymatic techniques for the detection, localization and quantitation of antigens and antibodies. This is described, for example, in J. Histochem. and Cytochem., Vol. 27, No. 8, 1131–1139 (1979), J. Histochem and Cytochem., Vol. 29, No. 4, 577–580 (1981), and Methods in Enzymology, Vol. 62, 308–315 (1979). In these prior art procedures, biotin is attached to a desired molecule by means of biotin-N-hydroxysuccinimide ester. The use of caproylamidobiotin-N-hydroxysuccinimide ester to attach biotin to an antibody is disclosed in Clin. Chem. 25/9, 1572–1580 (1979), and the resulting agglutination titer with respect to avidin was compared to biotinylated molecules prepared using biotin-N-hydroxysuccinimide ester. No difference in agglutination titer was seen. Caproylamidobiotinylated alkaline phosphatase and polymers thereof useful in DNA probes are disclosed in Proc. Natl. Acad. Sci. U.S.A., Vol. 80, 4045–4049 (July 1983).

It is known that biotinylated materials, such as biotinylated peroxidase, used in these prior art techniques can readily lose their ability to bond with avidin upon storage prior to eventual use in an immunochemical procedure.

There is no disclosure in the known prior art of caproylamidobiotinylated horseradish peroxidase or that such modified peroxidase would have improved storage stability and immunohistochemical functionality as compared to conventional prior art biotinylated peroxidase.

SUMMARY OF THE INVENTION

In accordance with the present invention, a novel compound, caproylamidobiotinylated horseradish peroxidase, is provided. This compound is useful as an element in immunoassay apparatus and as a process component in an immunoassay process.

DESCRIPTION OF THE INVENTION

The horseradish peroxidase used as a raw material for the production of the novel compound of the present invention is well known and is commercially available. This peroxidase dissolved in aqueous solution is reacted with caproylamidobiotin-N-hydroxysuccinimide ester dissolved in dimethylsulfoxide or dimethylformamide at room temperature for about 1–4 hours. The caproylamidobiotin-N-hydroxysuccinimide ester is prepared as described in Clin. Chem. 25/9, 1572–1580 (1979). The resulting reaction solution is purified by dialysis against phosphate buffered saline solution. A resulting impurity precipitate is separated conveniently by centrifugation to produce a clear supernatant liquid containing caproylamidobiotinylated horseradish peroxidase. The above-prepared caproylamidobiotinylated peroxidase can be used as an element in immunoassay apparatus and as a process component in an immunoassay process. In a known immunoassay process to detect a specific antigen, such as lambda and kappa immunoglobulins in tonsil sections, a primary antibody for such antigen, such as that produced in rabbits, is employed to bond the antigen. A biotinylated linking antibody, such as the biotinylated form of goat anti-rabbit IgG, is then bound to the primary antibody. Several process alternatives are then possible. In one variation, avidin is bound to the above linking antibody and a biotinylated peroxidase is then bound to the avidin. In another variation, a peroxidase-labeled avidin is bound to the linking antibody. In a third and preferred variation, the avidin is first reacted with biotinylated peroxidase to form a complex, and then this complex is bound to the linking antibody. In all these process variations the resulting bound peroxidase is then reacted with hydrogen peroxide and an oxidizable color-forming substrate or chromogen, such as 3-amino-9-ethylcarbazole or 3,3'-diaminobenzidine. The amount of color produced is thus directly related to the amount of antigens present and can be used to quantitatively and qualitatively measure such antigens.

Streptavidin, a commercially available biotin-binding protein produced from *Streptomyces avidinii* and also described in Arch. Biochem and Biophy., Vol. 106, 1–5 (1964), can be preferably used in place of avidin. When this technique is used to stain biological tissues to detect antigens therein, the streptavidin results in lower background staining. It is equally effective with avidin in binding to biotin.

An immunoassay apparatus or test kit employing the caproylamidobiotinylated peroxidase of the present invention can generally comprise a bottle containing the primary antibody for the specific antigen being measured, a bottle containing biotinylated linking antibody, a bottle containing avidin or streptavidin, a bottle containing caproylamidobiotinylated horseradish peroxidase, a bottle containing the chromogen, a bottle containing hydrogen peroxide and appropriate mixing bottles for the above reagents. Ancillary apparatus items that are known in the art, such as buffers, counterstains, slide and tissue processing apparatus and solutions, can also be used to carry out the desired procedure.

The invention is described in further detail in the following examples.

EXAMPLE 1

Phosphate buffered saline solution was prepared in the following manner. An 18.8 g. portion of anhydrous dibasic potassium phosphate was dissolved in 140 ml. distilled water preheated to 45° C. To this solution were added 3.3 g. monobasic sodium phosphate, and it was stirred until dissolved. Then 45 g. sodium chloride were added with stirring. After the sodium chloride was dissolved, the solution was brought to 200 ml. with distilled water. A 40 ml. portion of the above solution was then mixed with 960 ml. distilled water to form a 0.01M phosphate buffered saline solution (PBS) at pH 7.5. It was then stored at 4° C. Larger quantities were also prepared using the above proportions.

A 100 mg. portion of horseradish peroxidase powder was dissolved in 10 ml. of 0.1M carbonate/bicarbonate buffer at pH 9.0. Caproylamidobiotin-N-hydroxysuccinimide ester [prepared as described in Clin. Chem. 25/9, 1572–1580 (1979)] was dissolved in dimethylsulfoxide to a 0.1M concentration. A mixture of 10 ml. of the first solution and 2 ml. of the second solution was maintained at room temperature (about 20° C.) for 4 hours with occasional stirring. The resulting reaction solution was dialyzed at 0°14 4° C. against 500 ml. of PBS for 1 hour, then against a fresh batch of 500 ml. PBS for 1 hour and finally overnight against a fresh batch of 2 liters PBS. After dialysis was complete, the reaction solution was centrifuged at 20,000×g. for 10 min. to separate the precipitate formed during dialysis. The clear supernatant was removed and identified as "the new biotinylated horseradish peroxidase".

The above procedure was repeated using biotin-N-hydroxysuccinimide ester [prepared as described in Methods in Enzymology, Vol. 62, 308–315 (1979)] to prepare a clear supernatant identified as "the old biotinylated horseradish peroxidase".

Both of the above products were subjected to analyses to determine the catalytic activity and the biotin content. The peroxidase catalytic activity was measured by the procedure described in Methods of Enzymatic Analysis, Vol. 1, 494–495 (1974), 2nd. Ed., Verlag Chemie International, Deerfield Beach, Fla. The specific activity of the biotinylated enzymes was 240±30 units per mg. protein which was equal to that of the native or unbiotinylated forms of the enzyme. The biotin content was measured by spectrophotometric titration of the complex made up of avidin and 2-(4'-hydroxy-azobenzene)-benzoic acid as described in Biochem J., Vol 94, 23c–24c (1965). The results were stated as moles of biotin per mole of the enzyme using a molar extinction coefficient of the complex as 35,000 and an average molecular weight of the peroxidase as 40,000. "Avidin-accessible biotin" of the biotinylated enzyme is the number of moles of biotin per mole of enzyme determined directly by the above procedure. The total biotin content was expressed as the moles of biotin per mole of enzym determined by the above procedure after acid hydrolysis. Such acid hydrolysis was carried out in 6N hydrochloric acid in a sealed, evacuated tube at 110±5° C. overnight. Hydrochloric acid was removed at 40° C. under nitrogen and the residues were dissolved in PBS for subsequent biotin determinations. Biotin recovery after acid hydrolysis was about 73–81 mole percent.

Each of the "old" and "new" biotinylated horseradish peroxidase materials were then stored at 37° C. to check their storage stability. The "old" material was stored for 3 days while the "new" material was stored for 6 weeks. The respective biotin contents were then measured by the above-described procedures. The effects on the biotin content are shown in the following table.

TABLE 1

| | Moles of Biotin/Mole Enzyme | | | |
| | Initial | | After Storage | |
| Sample | Total | Avidin Accessible | Total | Avidin Accessible |
|---|---|---|---|---|
| Old | 3.5 | 1.5 | 4 | Not Detectable |
| New | 9.5 | 6.5 | 9.5 | 6.3 |

It can thus be seen that the caproylamidobiotinylated peroxidase contains a larger amount of biotin and is more storage stable than the prior art biotinylated peroxidase. The "avidin accessible" biotin is an expression of the amount of total biotin that is available for bonding to avidin. The higher this value, the higher is the expected functionality of the material to bond to avidin in a subsequent analytical procedure.

The utility of the new biotinylated horseradish peroxidase of the present invention in an immunohistochemical technique as well as the advantage of the new material over the prior art are shown in the following example.

EXAMPLE 2

Separate portions of the "new" and "old" biotinylated horseradish peroxidase both as prepared and after storage as described in Example 1 were each employed in the following procedure relating to staining antigens in human tissues. All of these process steps were carried out at room temperature.

A set of twenty slides each containing a 5 micrometer thick section of human tonsil tissue that had previously been fixed and paraffin embedded were processed in a commercial slide processor to remove the paraffin and to rehydrate the tissue. This processing comprised the steps of immersing the slides into successive 200 ml. portions of xylene, xylene, absolute ethanol, 95 volume percent aqueous ethanol, and 70 volume percent aqueous ethanol. The slides were immersed for 3 min. at each step. The slides were then rinsed in gently running tap water for 30 seconds. The slides were then immersed for 5 min. in 200 ml. of Lugol's Iodine Solution. (This was previously prepared by dissolving 12 g. potassium iodide in 20 ml. distilled water followed by dissolving 6 g. iodine in the same solution. The total volume was brought to 600 ml. with distilled water.) The slides were then rinsed in gently running tap water for 30 sec. The slides were then immersed in 200 ml. of 5 percent (weight/volume basis) aqueous sodium thiosulfate solution for 1 min. followed by rinsing in gently running tap water for 5 min. The above steps employing Lugol's Iodine and sodium thiosulfate were intended to remove any mercury salts that might be present and subsequently form undesirable black deposits in the subsequently stained sections. Any endogenous peroxidase-type activity that might be present in the tissue sections was then removed by immersing the slides in 200 ml. of 2 percent (weight/volume basis) aqueous hydrogen peroxide for 5 min. followed by immersion for 20 sec. each in two successive 200 ml. fresh portions of PBS. The excess liquid was removed from the slides by draining.

Each slide section was then separately covered with about 200 microliters of normal goat serum containing 270 micrograms serum solids and allowed to stand for 20 min. The serum was then removed by draining. Each slide section was then separately covered with about 200 microliters of rabbit anti-lambda antibodies solution containing 2.7 micrograms of immunoglobulins. This antibody material was commercially available. The slides were then allowed to stand for 20 min. and were then immersed for 20 sec. each in two successive 200 ml. fresh portions of PBS. The excess liquid was removed by draining. Each slide section was then separately covered with about 200 microliters of biotinylated goat antirabbit antibodies solution containing 0.5 micrograms of immunoglobulins. This antibody material was commercially available and was biotinylated according to the procedure in Journal of Histochem. and Cytochem. Vol. 29, No. 4, 577–580 (1981). The slides were then allowed to stand for 20 min. and were then immersed for 20 sec. each in two successive 200 ml. fresh portions of PBS. The excess liquid was removed by draining. A streptavidin-biotinylated peroxidase complex was previously prepared by the following procedure.

A 0.5 mg. portion of commercially available streptavidin powder was dissolved in 1 ml. PBS to form a streptavidin stock solution. A 100 microliters amount of such stock solution was mixed with 5 ml. PBS to form a diluted streptavidin solution. A 0.125 mg. portion of biotinylated horseradish peroxidase prepared as described above was dissolved in 1 ml. PBS to form a peroxidase stock solution. A 100 microliters amount of such stock solution was added to the above diluted streptavidin solution and allowed to stand for 20 min. to form a streptavidin-biotinylated peroxidase complex. Each slide section was then separately covered with about 200 microliters of the above prepared complex and allowed to stand for 20 min. They were then immersed for 20 sec. each in two successive 200 ml. fresh portions of PBS. The excess liquid was removed by draining. Each slide section was then separately covered with about 200 microliters of 0.05 percent (weight-/volume basis) 3-amino-9-ethylcarbazole and 0.025 percent (weight/volume basis) hydrogen peroxide in 0.0625 M acetate buffer and allowed to stand until a red color could be observed when monitored with a light microscope. This took about 15 min. The slides were then gently rinsed with distilled water followed by counterstaining by immersing in a commercially available solution of Mayer's hematoxylin for 5 min. The slides were then gently rinsed with distilled water followed by immersion in 200 ml. aqueous ammonia water. This was previously prepared by mixing 2 ml. concentrated ammonium hydroxide (about 14.8 M) with 1 liter of tap water. The slides were dipped ten times in the ammonia water followed by rinsing under gently running tap water for 5 min. The slides were then coverslipped using liquid glycerol gelatin.

The resulting stained tissue sections were microscopically examined with respect to color intensity, background staining and antigen distribution. The immunohistochemical functions of the various biotinylated peroxidases were then scored on an arbitrary scale of 0–4+ with 0 being the minimum and 4+ being the maximum. The results are shown in the following table.

TABLE 2

| Sample | Immunohistochemical Function | |
| --- | --- | --- |
|  | Initial | After Storage |
| Old | 1–2+ | Not detectable |
| New | 4+ | 4+ |

It can thus be seen that the caproylamidobiotinylated peroxidase has a higher immunohistochemical functionality and retains such functionality for a longer time then the prior art biotinylated peroxidase.

What is claimed is:

1. Caproylamidobiotinylated horseradish peroxidase.
2. Immunoassay apparatus containing as an element the caproylamidobiotinylated horseradish peroxidase of claim 1.
3. An immunoassay process employing as a process component the caproylamidobiotinylated horseradish peroxidase of claim 1.

* * * * *